United States Patent
Koch

[19]

[11] Patent Number: 6,050,140
[45] Date of Patent: Apr. 18, 2000

[54] ADHESION TESTER

[75] Inventor: Frank J. Koch, Ogdensburg, N.Y.

[73] Assignee: Defelsko Corporation, Ogdensburg, N.Y.

[21] Appl. No.: 09/126,716

[22] Filed: Jul. 31, 1998

[51] Int. Cl.[7] .................................................. G01N 19/04
[52] U.S. Cl. ............................ 73/150 A; 73/827; 73/834
[58] Field of Search .............................. 73/150 A, 150 R, 73/827, 830, 834, 838

[56] References Cited

U.S. PATENT DOCUMENTS

| | | |
|---|---|---|
| 3,527,093 | 9/1970 | Sellers . |
| 3,821,892 | 7/1974 | Saberg . |
| 4,491,014 | 1/1985 | Seiler, Jr. . |
| 4,567,758 | 2/1986 | Fisher et al. ........................... 73/150 A |
| 4,586,371 | 5/1986 | Ivie et al. . |
| 4,606,225 | 8/1986 | Thomason et al. .................... 73/150 A |
| 4,862,740 | 9/1989 | Lanier ..................................... 73/150 A |
| 4,876,896 | 10/1989 | Snow et al. . |
| 5,361,639 | 11/1994 | Thorsen . |
| 5,649,447 | 7/1997 | Avery ...................................... 73/150 A |

FOREIGN PATENT DOCUMENTS

| | | |
|---|---|---|
| 2655148 | 5/1991 | France . |
| 317 959 | of 1971 | Russian Federation . |
| 642 630 | 1/1979 | Russian Federation . |
| 379 243 | 7/1972 | Sweden . |
| 1 455 534 | 10/1976 | United Kingdom . |
| 2 196 437 | 4/1988 | United Kingdom . |
| 2 270 769 | 3/1994 | United Kingdom . |

*Primary Examiner*—Max Noori
*Attorney, Agent, or Firm*—Burns, Doane, Swecker & Mathis LLP

[57] ABSTRACT

An adhesion tester includes a dolly to be adhered to a coating to be tested; the dolly including at least a portion of a spherical surface; a frame having a hollow portion in a region thereof, in which region the dolly fits; a hydraulic piston within the frame; and a quick connect coupler for connecting the hydraulic piston to the dolly; the coupler including a plurality of ball bearings aligned so as to engage with a lower half of the spherical surface of the dolly so as to connect the dolly with the coupler.

27 Claims, 2 Drawing Sheets

ADHESION TESTER

BACKGROUND OF THE APPLICATION

1. Field of the Invention

The present invention relates to a device for testing the adhesive qualities of a coating, and more particularly, to a pneumatic or hydraulic device for carrying out tests, such as measuring the adhesive properties of a coating on a substrate, or tensile testing of materials that possess little elasticity.

2. Discussion of Related Art

Devices for testing the adhesion of a coating, e.g., paint or adhesives, to an underlying surface have been known for many years. The accurate testing of the adhesion of a material has importance to many industries. It is therefore important to have a device that provides accurate and consistent results.

Many of the prior art devices utilize a dolly that is fixed by an adhesive to a coating on an underlying substrate to test the adhesion strength between the substrate and the applied coating. A frame engages the dolly and applies a force to the dolly that is perpendicular to the substrate. The amount of force that is applied to the dolly to make the coating separate from the substrate corresponds to the adhesive strength of the coating to the substrate.

Several of the prior art devices engage the dolly with a structure that a has a plurality of legs that surround the dolly. The legs engage the coating on which the dolly is secured and apply a counteracting force to the coating. A problem with such devices is if the force is not applied evenly to all of the legs, the applied tensile force may be applied unevenly to the dolly. If the force is not applied evenly to the dolly, the coating between the dolly and the substrate may begin to yield at only one edge of the dolly, thus providing an inaccurate reading.

To overcome this problem, some of the prior art devices apply means for adjusting the length of the legs supporting the refracting device. Other devices rely on a pneumatic or hydraulic system that applies a pressure to all of the legs uniformly. See, e.g., U.S. Pat. No. 5,361,639.

However, such devices do not provide a self-centering device that engages the test dolly. Accordingly, even if the pressure is applied evenly to all of the legs, and if all of the legs are adjusted to the same length, if the dolly is skewed at a slight angle, the adhesion tester still may apply a force such that the coating tends to separate from the substrate at one edge thereof.

Other prior art devices provide an opening in the center of the doily through which a pin is used to apply a force against the coating. A problem with such a structure is that the dolly does not have an uninterrupted surface area that is adhered to the coating.

OBJECTS AND SUMMARY

Accordingly, it is an object of the present invention to provide an adhesion tester that applies a retractile force to a dolly to separate the dolly from a substrate in such a manner such that the dolly is lifted uniformly off of the substrate.

It is another object of the present invention to provide an adhesion tester that provides consistently accurate results.

It is yet another object to provide an adhesion tester that provides an uninterrupted area on a dolly for adhesion.

According to one embodiment of the present invention, an adhesion tester includes a dolly to be adhered to a coating to be tested, the dolly including an inclined peripheric surface extending circumferentially around an outside edge of the dolly; a frame having a portion for receiving the dolly; a hydraulic piston within the frame; and a coupler for connecting the hydraulic piston to the dolly. The coupler includes a plurality of low friction contact points for engaging with the inclined peripheric surface of the dolly while enabling relative pivoting movement between the coupler and the dolly.

According to another aspect of the present invention, an adhesion tester includes a dolly to be adhered to a coating to be tested, a frame having a portion for receiving the dolly, and a hydraulic piston within the frame, a coupler for connecting the hydraulic piston to the dolly, and means for enabling the coupler to engage the dolly in a self-centering manner while enabling relative pivoting movement between the coupler and the dolly. The enabling means includes an inclined peripheric surface on the dolly and low friction contact points on the coupler.

According to yet another aspect of the present invention, the coupler includes a plurality of ball bearings aligned so as to engage with a lower half of the spherical surface of the dolly so as to connect the dolly with the coupler.

DETAILED DESCRIPTION OF THE PREFERRED EMBODIMENTS

Figure 1:
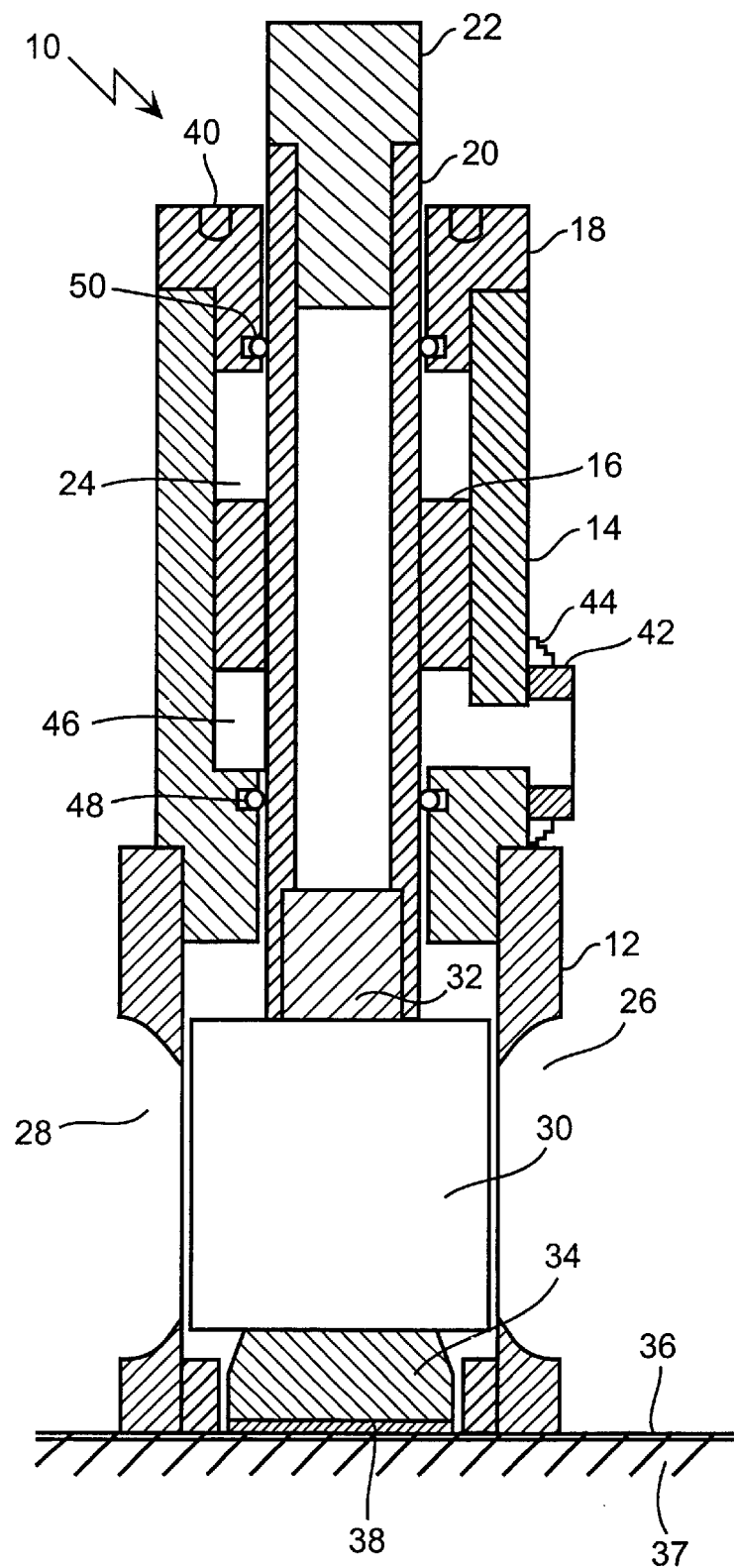
FIG. 1 is a cross-sectional view of an embodiment of the adhesion tester of the present invention.

FIGS. 1–4 illustrate a preferred, exemplary embodiment of an adhesion tester in accordance with the present invention. The adhesion tester 10 is used to test the adhesive strength of a coating 36 on a substrate 37.

The adhesion tester 10 includes a main frame that has a quick connect coupler 30 secured therein. The quick connect coupler 30 is used to detachably engage with a dolly 34. The tester 10 includes a cylindrical base portion 12 that is threadably engaged with an upper cylindrical portion 14. The base portion 12 is intended to stand on the coating 36. The upper cylindrical portion 14 includes an internal chamber 46. The chamber 46 is closed by a cap 18.

An inlet 42 extends through the upper cylindrical portion 14 to enable pneumatic, or alternatively hydraulic, fluid to be applied into the chamber 46. A weld 44 may surround the inlet 42.

A piston rod 20 having a piston 16 secured fixedly thereto is slidably mounted within the upper cylindrical portion 14 and the cap 18. A substantially fluid tight seal is created between the piston rod 20 and the cap 18 by means of an 0-ring 50 at the top end of the chamber 46. In addition, a second 0-ring 48 provides a substantially fluid tight seal at the lower end of the cylindrical portion 14 between the upper cylindrical portion 14 and the piston rod 20.

At the top of the piston rod 20 is a head 22. A button 80, illustrated in FIG. 4, includes a recess 82. The button 80 is mounted onto the head 22 with the recess 82.

The cap 18 may be joined to the upper cylindrical portion 14 by any means known to those of skill in the art. In a preferred, exemplary manner, the cap 18 is threaded into the upper end of the upper cylindrical portion 14. Recesses 40 are provided at a top surface of the cap 18 so that the cap 18 may be rotated with respect to the upper cylindrical portion 14 by means of a spanner wrench.

The upper cylindrical portion 14 may be joined to the lower cylindrical portion 12 by any means known to those of skill in the art. In a preferred, exemplary embodiment, the upper cylindrical portion 14 is threadably engaged into the lower cylindrical base 12.

Figure 3:
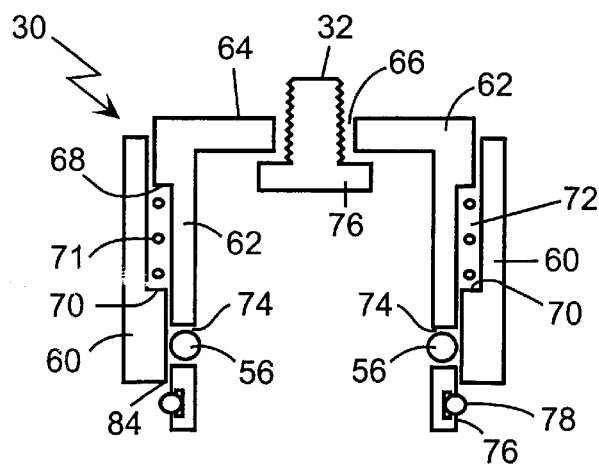
FIG. 3 is a cross-sectional view of a quick connect coupler to be used with the adhesion tester of FIG. 1.
Figure 4:
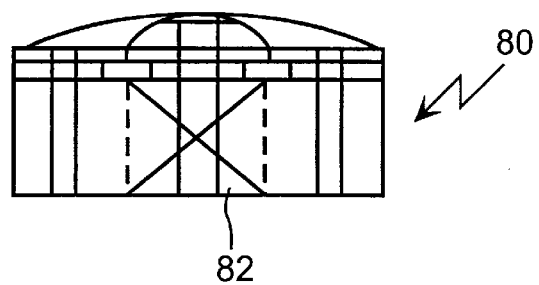
FIG. 4 is a side elevational view of a cap to be used at the top of the adhesion tester of FIG. 1.

At a lower end of the piston rod 20, a bolt 32 is threadably secured into the piston rod 20. See FIGS. 1 and 3. The bolt 32 is used to fasten the quick connect coupler 30 to the lower end of the piston rod 20. Turning attention now to FIG. 3, the quick connect coupler 30 includes an outer sleeve 60 and an inner sleeve 62 that is concentrically arranged within the outer sleeve 60. The inner sleeve 62 includes a top surface 64 having an opening 66 extending therethrough. The bolt 32 includes a head 76 that is too large to pass through the opening 66. Accordingly, the inner sleeve 62 can be secured to the lower end of the piston rod 20 by threadably engaging the nut 32 into threads in a lower portion of the piston rod 20.

However, the inner sleeve 62 of the quick connect coupler 30 may include an integral threaded projection, instead of the bolt 32, for engaging the quick coupler 30 to the piston rod 20.

The inner sleeve 62 includes a shoulder 68 that confronts a shoulder 70 of the outer sleeve 60. An annular space 72 is created between the inner sleeve shoulder 68 and the outer sleeve shoulder 70. A coil spring 71, or comparable biasing mechanism, is located in the annular space 72 in order to bias the outer sleeve 60 downwardly, with respect to the inner sleeve, at least with respect to the FIG. 3 view.

The inner sleeve 62 includes a plurality of openings 74, and a ball bearing 56 is arranged in each of the openings 74. Although not detectable from the drawings, each of the openings 74 is slightly tapered so that the ball bearings 56 can only fit into the openings 74 from the outside of the inner sleeve.

The inner sleeve 62 further includes an annular recess 76 at a bottom end thereof. A split ring 78 is placed in the recess 76 in order to retain the outer sleeve 60 in place on the inner sleeve 62.

When the outer sleeve 60 is in the position illustrated in FIG. 3, i.e., biased against the ring 78 of the inner sleeve 62, the inner wall of the outer sleeve 60 maintains the ball bearings in a position such that they project inwardly from the inner sleeve 62. However, if the outer sleeve 60 is urged upwardly, against the bias of the spring 71, the ball bearings 56 are able to move outwardly, such that they do not extend inwardly any further than an inner surface of the inner sleeve 62. Upward movement of the outer sleeve 60 is limited such that a lower corner 84 of the outer sleeve 60 prevents the ball bearings 56 from completely leaving the openings 74.

Figure 2:
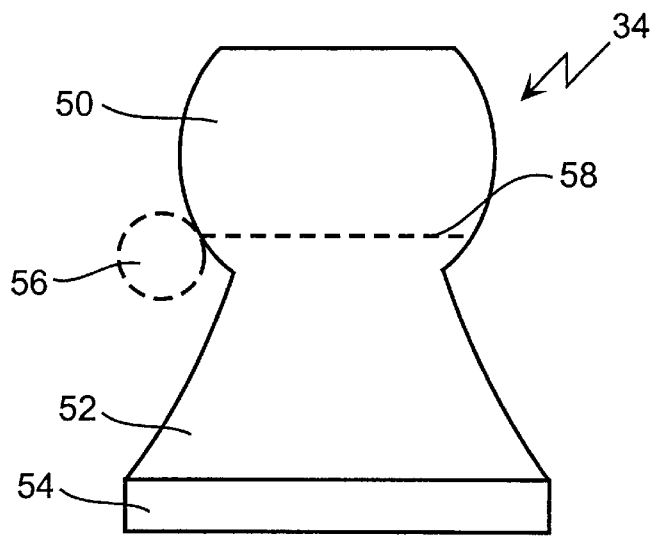
FIG. 2 is a side elevational view of a dolly to be used with the adhesion tester of FIG. 1.

In operation, the dolly 34, illustrated in FIGS. 1 and 2, is adhered to a coating 36 with an adhesive 38. The adhesive 38 may be either an epoxy or an instant adhesive that preferably has stronger adhesive qualities than the coating to be tested. With the quick connect coupler 30 previously engaged to the piston rod 20 by means of the bolt 32, the frame 10 is placed over the dolly 34.

The lower cylindrical base portion 12 of the frame 10 includes cutouts 26, 28 on opposite sides thereof. An operator of the adhesion tester reaches through the cutouts 26, 28, and raises the outer sleeve 60 of the quick connect coupler 30 so that the ball bearings 56 may move outwardly. In this position, the ball bearings 56 are able to slide over the spherical head 50 of the dolly 34. Once the ball bearings 56 are at or below a contact level 58 of the sphere 50 of the dolly 34, the outer sleeve 60 of the quick connect coupler 30 may be released. At this point, the spring 71 will urge the outer sleeve 60 downwardly, thus forcing the ball bearings 56 inwardly.

The ball bearings 56 are forced inwardly to such an extent that the ball bearings 56 cause the quick connect coupler 30 to engage the dolly 34, and prevent the dolly 34 from separating from the coupler 30.

In view of the fact that the dolly 34 has a spherical head 50, if, for some reason, the frame 10 is not perfectly symmetrical or in alignment with the dolly 34, the ball bearings 56 will enable the dolly 34 to pivot with respect to the coupler to automatically center itself in an appropriate location on the spherical head 50 such that an even, concentric force will be applied to the dolly 34. Thus, the quick connect coupler 30 is self-centering with respect to the dolly 34.

A source of pneumatic or hydraulic fluid (not shown) is attached to the inlet 42. The inlet 42 is directly open to the inner chamber 46 of the upper cylindrical portion 14 of the adhesion tester. Fluid pressure is then applied to the inlet 42, thus increasing the pressure in the portion of the chamber 46 below the piston 16. The fluid pressure urges the piston 16 in an upward direction. Since the piston 16 is fixed to the piston rod 20, and the quick connect coupler 30 is secured to the lower end of the piston rod 20, the fluid pressure applies an upward force to the quick connect coupler 30. This upward force is in turn transmitted to the dolly 34. When sufficient pressure has been applied to separate the coating 36 from the substrate 37, which is an indication of adhesive strength, a reading of the pressure is taken. Means for taking the pressure reading are well known to those of ordinary skill in this art.

In view of the spherical nature of the head 50 of the dolly, the upward pressure will always be exerted on the dolly 34 in a manner that is spread uniformly around the dolly 34. Thus, there is no concern of the coating being lifted off of the substrate 37 by only one edge thereof. Accordingly, it is possible to get consistent, uniform results.

After the coating 36 has separated from the substrate 37, and the pressure reading has been taken, a downward pressure is applied on the cap 80, thus urging the piston 16 and piston rod 20 in a downward direction.

By manually raising the outer sleeve 60 of the quick connect coupler 30, the adhesion tester 10 can be removed from the dolly 34.

Although the embodiment disclosed above includes a piston for applying the retractive force to the coupler, other means for applying the force may be utilized. For example, a screw system could be utilized wherein the inside surface of the frame includes threads, and a bolt is arranged within the threads. A lower end of the bolt is attached to the coupler. A retractive force is applied by unscrewing the bolt.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. An adhesion tester, comprising:
a dolly to be adhered to a coating to be tested;

the dolly including an inclined peripheric surface extending circumferentially around an outside edge of the dolly;
a frame having a portion for receiving the dolly;
means for applying a retractive force between the frame and the dolly; and
a coupler for connecting the applying means to the dolly;
the coupler including a plurality of low friction contact points for engaging with the inclined peripheric surface of the dolly while enabling relative pivoting of the coupler with respect to an axial direction of the dolly.

2. The adhesion tester of claim 1, wherein the contact points are spherical ball bearings and the inclined surface has a radius that is greater than a radius of the ball bearings.

3. The adhesion tester of claim 1, wherein the inclined surface constitutes a truncated sphere.

4. The adhesion tester of claim 3, wherein the contact points are spherical ball bearings.

5. The adhesion tester of claim 3, wherein the coupler is a quick release coupler.

6. The adhesion tester of claim 1, wherein the applying means includes a hydraulic piston.

7. The adhesion tester of claim 1, wherein the applying means includes a pneumatic piston.

8. An adhesion tester, comprising:
a dolly to be adhered to a coating to be tested;
the dolly including an inclined annular surface extending circumferentially around an outside edge of the dolly, said surface having a predetermined height with respect to an axis of the dolly;
a frame having a portion for receiving the dolly;
means for applying a retractive force between the frame and the dolly; and
a coupler for connecting the applying means to the dolly;
the coupler including a plurality of low friction contact points for engaging with the inclined annular surface of the dolly so as to connect the dolly with the coupler, the contact points having a dimension that is less than the predetermined height so as to enable relative pivoting of the coupler with respect to an axial direction of the dolly by moving the contact points along the annular surface.

9. The adhesion tester of claim 8, wherein the contact points are spherical ball bearings and the inclined surface has a radius that is greater than a radius of the ball bearings.

10. The adhesion tester of claim 8, wherein the inclined surface constitutes a truncated sphere.

11. The adhesion tester of claim 10, wherein the contact points are spherical ball bearings.

12. The adhesion tester of claim 8, wherein the coupler is a quick release coupler.

13. The adhesion tester of claim 8, wherein the applying means includes a hydraulic piston.

14. The adhesion tester of claim 8, wherein the applying means includes a pneumatic piston.

15. An adhesion tester, comprising:
a dolly to be adhered to a coating to be tested;
a frame having a portion for receiving the dolly;
means for applying a retractive force between the frame and the dolly; and
a coupler for connecting the applying means to the dolly; and
means for enabling the coupler to engage the dolly in a self-centering manner by enabling relative pivoting of the coupler with respect to an axial direction of the dolly, said means including an inclined peripheric surface on the dolly and low friction contact points on the coupler.

16. The adhesion tester of claim 15, wherein the contact points are spherical ball bearings and the inclined surface has a radius that is greater than a radius of the ball bearings.

17. The adhesion tester of claim 15, wherein the inclined surface constitutes a truncated sphere.

18. The adhesion tester of claim 17, wherein the contact points are spherical ball bearings.

19. The adhesion tester of claim 15, wherein the coupler is a quick release coupler.

20. The adhesion tester of claim 15, wherein the applying means includes a hydraulic piston.

21. The adhesion tester of claim 15, wherein the applying means includes a pneumatic piston.

22. An adhesion tester, comprising:
a dolly to be adhered to a coating to be tested;
the dolly including at least a portion of a spherical surface;
a frame having a hollow portion in a region thereof in which region the dolly fits;
a hydraulic piston within the frame; and
a quick connect coupler for connecting the hydraulic piston to the dolly;
a coupler for connecting the applying means to the dolly; and
the coupler including a plurality of ball bearings aligned so as to engage with a lower half of the spherical surface of the dolly so as to connect the dolly with the coupler.

23. The adhesion tester of claim 22, wherein the spherical surface has a radius that is greater than a radius of the ball bearings.

24. An adhesion tester according to claim 1, wherein:
the dolly includes a body portion extending along a longitudinal axis and the low friction contact points engage the inclined peripheral surface of the dolly to allow a limited range of relative motion between the contact points and the inclined peripheral surface in an axial direction.

25. An adhesion tester according to claim 8, wherein:
the dolly includes a body portion extending along a longitudinal axis and the low friction contact points have a dimension along the longitudinal axis that is less than the predetermined height of the inclined annular surface of the dolly, thereby allowing a limited range of relative motion between the contact points and the inclined peripheral surface in an axial direction.

26. An adhesion tester according to claim 15, wherein:
the low friction contact points on the coupler are adapted to allow relative motion in an axial direction along the inclined peripheral surface of the dolly.

27. An adhesion tester, comprising:
a frame defining a shaft extending along a longitudinal axis and a chamber for receiving a fluid under pressure;
a piston rod slideably engaged with a portion of the shaft and moveable along the longitudinal axis between a first position and a second position; and
a dolly pivotally mounted to the piston rod and having a surface adapted to be adhered to a coating of an underlying substrate when the piston rod is in the first position,
such that pressurized fluid introduced into the chamber exerts a force on the piston rod in a direction of the longitudinal axis, the force being translated through the dolly to the coating of the underlying substrate.

* * * * *